US012758255B2

(12) United States Patent
Vogt et al.

(10) Patent No.: US 12,758,255 B2
(45) Date of Patent: Oct. 13, 2026

(54) MRI-CT-COMPATIBLE REMOTE-CONTROLLED MICROPOSITIONING SYSTEM

(71) Applicants: Otto-von-Guericke-Universität Magdeburg, Magdeburg (DE); Medizinische Hochschule Hannover, Hannover (DE)

(72) Inventors: Ivan Vogt, Magdeburg (DE); Robert Odenbach, Magdeburg (DE); Bennet Hensen, Hannover (DE); Enrico Pannicke, Magdeburg (DE)

(73) Assignees: Otto-von-Guericke-Universität Magdeburg, Magdeburg (DE); Medizinische Hochschule Hannover, Hannover (DE)

( * ) Notice: Subject to any disclaimer, the term of this patent is extended or adjusted under 35 U.S.C. 154(b) by 407 days.

(21) Appl. No.: 18/564,380

(22) PCT Filed: May 30, 2022

(86) PCT No.: PCT/EP2022/064591
§ 371 (c)(1),
(2) Date: Dec. 13, 2023

(87) PCT Pub. No.: WO2022/253747
PCT Pub. Date: Dec. 8, 2022

(65) Prior Publication Data

US 2024/0238006 A1 Jul. 18, 2024

(30) Foreign Application Priority Data

May 31, 2021 (DE) .................... 10 2021 113 953.8

(51) Int. Cl.
*A61B 17/34* (2006.01)
*A61B 90/00* (2016.01)
*A61B 17/00* (2006.01)

(52) U.S. Cl.
CPC .......... *A61B 17/3403* (2013.01); *A61B 90/39* (2016.02); *A61B 2017/00212* (2013.01);
(Continued)

(58) Field of Classification Search
CPC ..... A61B 17/3403; A61B 90/11; A61B 90/39; A61B 2017/00212; A61B 2017/3407;
(Continued)

(56) References Cited

U.S. PATENT DOCUMENTS 7,313,430 B2 * 12/2007 Urquhart ................ A61B 34/20 600/428
7,824,417 B2 * 11/2010 Magnusson ........ A61B 17/3403 606/130

(Continued)

FOREIGN PATENT DOCUMENTS

DE 102008051111 A1 4/2010
DE 102020104746 B3 6/2021

(Continued)

OTHER PUBLICATIONS

International Search Report from corresponding International Patent Application No. PCT/EP22/64591, dated Sep. 23, 2022.

*Primary Examiner* — Ryan J. Severson
(74) *Attorney, Agent, or Firm* — Renner, Otto, Boisselle & Sklar, LLP

(57) ABSTRACT

The invention relates to a positioning device for positioning a medical instrument relative to a patient, wherein the positioning device has a patient fastening member which is specified to fasten the positioning device to the patient, and has an instrument holder which is specified to hold the
(Continued)

medical instrument, wherein the patient fastening member has a patient holding surface for bearing on the patient.

12 Claims, 10 Drawing Sheets

(52) U.S. Cl.
CPC ................. *A61B 2017/3407* (2013.01); *A61B 2017/3409* (2013.01); *A61B 2090/3954* (2016.02)

(58) Field of Classification Search
CPC ...... A61B 2017/3409; A61B 2090/374; A61B 2090/3762; A61B 2090/3954; A61B 2090/3966; A61B 34/71; A61B 10/0233; A61B 2034/304
See application file for complete search history.

(56) References Cited

U.S. PATENT DOCUMENTS

| | | | | |
|---|---|---|---|---|
| 8,195,272 | B2 * | 6/2012 | Piferi | G01R 33/3415 128/845 |
| 8,644,906 | B2 * | 2/2014 | Piferi | G01R 33/285 600/410 |
| 9,222,996 | B2 * | 12/2015 | Fujimoto | G01R 33/286 |
| 9,387,008 | B2 * | 7/2016 | Sarvestani | A61B 17/3403 |
| 9,877,787 | B2 * | 1/2018 | Brabrand | A61B 90/11 |
| 10,441,377 | B2 * | 10/2019 | Rau | A61B 90/11 |
| 10,610,325 | B2 * | 4/2020 | Kato | A61B 17/3403 |
| 10,675,099 | B2 * | 6/2020 | Nakamura | A61B 34/20 |
| 10,702,257 | B2 * | 7/2020 | Hess | A61B 17/0218 |
| 10,933,223 | B2 * | 3/2021 | Rauniyar | A61B 17/3403 |
| 11,020,201 | B2 * | 6/2021 | Vogele | A61B 17/00234 |
| 11,096,758 | B2 * | 8/2021 | Morey | A61B 90/11 |
| 11,213,315 | B2 * | 1/2022 | Kincaid | A61B 17/3403 |
| 11,484,335 | B2 * | 11/2022 | Feng | A61M 5/3287 |
| 11,617,621 | B2 * | 4/2023 | Daniels | G16H 30/40 600/424 |
| 2004/0243146 | A1 * | 12/2004 | Chesbrough | A61B 90/11 604/385.06 |
| 2004/0260312 | A1 * | 12/2004 | Magnusson | A61B 17/3403 606/129 |
| 2005/0049486 | A1 | 3/2005 | Urquhart et al. | |
| 2006/0229641 | A1 * | 10/2006 | Gupta | A61B 17/3403 606/130 |
| 2012/0022368 | A1 * | 1/2012 | Brabrand | A61B 90/11 600/427 |
| 2013/0066192 | A1 | 3/2013 | Sarvestani et al. | |
| 2014/0275979 | A1 | 9/2014 | Fujimoto et al. | |
| 2014/0336670 | A1 * | 11/2014 | Brabrand | A61B 90/11 606/130 |
| 2016/0367332 | A1 | 12/2016 | Shah et al. | |
| 2017/0086813 | A1 * | 3/2017 | Hess | A61B 17/3462 |
| 2018/0008367 | A1 * | 1/2018 | Rau | A61B 17/17 |
| 2018/0093076 | A1 * | 4/2018 | Rauniyar | A61B 17/3415 |
| 2018/0228568 | A1 * | 8/2018 | Kato | A61B 90/11 |
| 2018/0338812 | A1 * | 11/2018 | Morey | A61B 17/3403 |
| 2019/0046233 | A1 * | 2/2019 | Feng | A61M 5/3287 |
| 2019/0090953 | A1 | 3/2019 | Nakamura | |
| 2019/0282263 | A1 * | 9/2019 | Kincaid | A61B 90/11 |
| 2020/0038110 | A1 * | 2/2020 | Daniels | G06T 7/0012 |
| 2021/0290316 | A1 * | 9/2021 | Ng | A61B 34/30 |
| 2024/0238006 | A1 * | 7/2024 | Vogt | A61B 34/71 |

FOREIGN PATENT DOCUMENTS

| | | | |
|---|---|---|---|
| EP | 3363392 | A1 | 8/2018 |
| WO | WO2020/005165 | A1 | 1/2020 |
| WO | WO2020/022951 | A1 | 1/2020 |

* cited by examiner

MRI-CT-COMPATIBLE REMOTE-CONTROLLED MICROPOSITIONING SYSTEM

FIELD OF THE INVENTION

The present invention relates generally to the field of medical apparatuses, in particular to the sector of imaging-supported interventions such as, for example, interventional magnetic resonance tomography (iMRT). More specifically, the invention relates to a positioning device for the preferably remote-controlled positioning of a medical instrument relative to a patient, wherein the positioning device has a patient fastening member which, by way of a patient holding surface, is specified to fasten the positioning device to a patient, and has an instrument holder which is specified to hold and displace, preferably by remote control, the medical instrument.

BACKGROUND OF THE INVENTION

In magnetic resonance tomography, there are particular requirements, for example in terms of the MRT-compatibility of the materials used in the medical apparatus and in terms of the ease of operation of medical devices on a patient in a relatively long and narrow MRT tunnel. Moreover, unnecessary stress acting on the people working in this sector due to the magnetic field (concentrated work in an intensive magnetic field), as well as due to the unfavorable ergonomic conditions (maintaining the position of extremities, e.g. stretching out an arm, over a long time), is to be avoided. Furthermore, the current daily routine in iMRT includes non-standardized operative steps, also referred to as workflows. This leads to there being a generally relatively low level of efficiency in terms of feasibility, and inexperienced interventionists tend to find it hard to enter the field of interventional processes.

For example, simple mechanical positioning aids which allow a biopsy needle or similar instrument to be guided and can be adjusted by the user substantially in terms of the angular orientation already exist for such applications in the iMRT sector. However, such devices cannot be remotely operated or aligned, but only offer a holding function.

SUMMARY OF THE INVENTION

The invention is based on the object of specifying an improved and remote-controlled positioning device for positioning a medical object (e.g. instrument, e.g. biopsy needle), which avoids the disadvantages mentioned above.

In a positioning device of the type mentioned at the outset, this object is achieved in that the instrument holder is connected to the patient fastening member via a rotary mechanism by way of which the instrument holder is mounted in an axis orthogonal to the patient holding surface so as to be rotatable, and thus able to be twisted, relative to the patient fastening member.

Such a positioning device has the advantage that a precise and reproducible adjustment of the direction of action or of the angle of attack of the medical instrument relative to the patient can be carried out, at least about the orthogonal axis (z-axis). Since the medical instrument and/or the instrument holder during an intervention is typically not aligned along the orthogonal axis but at an angle thereto, the medical instrument can be twisted at least in a specific angular range about the orthogonal axis by way of such a positioning device. If the medical instrument contains a needle, for example, the puncturing direction of the needle into the patient about the orthogonal axis can be changed by the positioning device. The positioning device can be designed in such a manner that an angle of rotation about the orthogonal axis of approximately 360°, or alternatively more than 360° or less than 360°, is made possible by the rotary mechanism.

The positioning device can be attached to the patient in a defined manner by the patient fastening member, said attachment maintaining the chosen attachment position and thus contributing toward a high reproducibility of the adjustment possibilities of the positioning device. For example, the patient holding member can be fastened to the patient by way of single-sided or double-sided adhesive tapes and/or by straps. The positioning of the patient holding member on the patient in this fixing does not have to be immediately precise, but can initially be performed in a relatively rough manner according to the individual judgement of the user above the targeted intervention area, because the positioning device offers additional degrees of freedom for compensating initial positional deviations.

According to an advantageous design embodiment of the invention it is provided that the instrument holder is coupled to the patient fastening member via a pivoting mechanism by way of which the angular position of the instrument holder is adjustable in relation to the patient holding surface. The instrument holder herein can be coupled indirectly to the patient fastening member by way of the pivoting mechanism, e.g. by way of the intervening rotary mechanism. This has the advantage that a precise and reproducible adjustment of the instrument holder, and thus of the instrument, in terms of the angular position in relation to the patient holding surface can additionally be carried out by the positioning device. In combination with the rotary mechanism about the orthogonal axis, an adjustment in two rotational degrees of freedom is already provided in this way, so that the angle of attack of the instrument in relation to the patient can be adjusted in a further angular dimension. The potential adjustment angle of the pivoting mechanism can be restricted to the ranges expedient for the practical application, i.e. to at most 180°, whereby a restriction to an angle of ±75° in terms of the orthogonal axis in relation to the patient's body is also sufficient in many cases.

The imaginary, or virtual, axis about which the pivoting mechanism is pivoted in this way can advantageously be designed in such a way that this axis lies horizontally on the patient's surface, in that the virtual center of the radius of the pivot arc is constructed to be on the patient's surface. With the instrument being guided in the rotary mechanism and in the pivoting mechanism, this thus creates an intersection point of the orthogonal axis and the horizontal axis, which intersection point is situated at all times true to its position on the patient's surface and in the center of the positioning device, independently of the current rotational or pivoted orientation of the instrument. This intersection point is the puncture point on the patient, and is advantageously true to its location so that the instrument can still be readjusted in terms of the rotating and pivoting angle even immediately after the skin surface has been punctured, without having to determine a new puncture point.

According to an advantageous design embodiment of the invention it is provided that the pivoting mechanism, conjointly with the instrument holder, by way of the rotary mechanism is able to be twisted about the axis orthogonal to the patient holding surface relative to the patient fastening member. This has the advantage that a rotational angular position set by means of the rotary mechanism does not have to be readjusted when the angular position of the pivoting mechanism is adjusted.

According to an advantageous design embodiment of the invention it is provided that the instrument holder is coupled to the patient fastening member via a displacement mechanism by way of which the instrument holder is displaceable in one or a plurality of directions in a plane parallel to the quasi-planar patient holding surface. This has the advantage that a precise and reproducible adjustment of the instrument holder in terms of a displaceability in the plane parallel to the patient holding surface can additionally be carried out by the positioning device. In this way, one or two additional translatory degrees of freedom of the adjustability on quasi-planar patient surfaces, for example on the thorax region, back region and abdominal region, can likewise be implemented, for example. As a result, the puncture location can be subsequently corrected or adapted if required, for example after an initially imprecise fixing of the patient fastening member above the desired puncture location on the patient.

According to an advantageous design embodiment of the invention it is provided that the rotary mechanism by way of the displacement mechanism is displaceable in one or a plurality of directions in the plane parallel to the patient holding surface. This has the advantage that a rotational angular position adjusted by means of the rotary mechanism does not have to be readjusted when adjusting the displacement mechanism.

According to an advantageous design embodiment of the invention it is provided that the pivoting mechanism by way of the displacement mechanism is displaceable in one or a plurality of directions in the plane parallel to the patient holding surface. This has the advantage that an angular position adjusted by means of the pivoting mechanism does not have to be readjusted when adjusting the displacement mechanism.

According to an alternative design for intervention regions on the patient which are not quasi-planar (e.g. on the shoulder joint, knee joint, or on the skull), the patient fastening member having the integrated displacement mechanism can be shaped so as not to be planar but cylindrical or spherical in such a way that the rotary mechanism and the pivoting mechanism of the positioning device are displaceably mounted on a cylinder shell or a spherical shell above the intervention region. The radii of the cylinder or sphere can be designed so as to vary in size, corresponding to the field of application, so that the puncture location of the instrument is (almost) permanently situated on the patient's surface, even when the rotary mechanism and the pivoting mechanism are displaced in the curved displacement mechanism, and is not virtually lifted from said patient's surface when displaced, such as is the case when a planar displacement mechanism is utilized on an anatomically curved surface.

According to an advantageous design embodiment of the invention it is provided that the instrument holder, or a component of the positioning device that is connected thereto, is releasably connected to the patient fastening member by way of a releasable connection, in particular a bayonet connection. This has the advantage that the instrument, conjointly with the instrument holder, can be easily removed and replaced, while the positioning device by way of the patient fastening member thereof is fastened to the patient and can remain fastened thereto. It is also possible that the instrument remains on the patient. The positioning device therefore does not have to be removed from the patient first. For example, the instrument holder, the rotary mechanism, the pivoting mechanism and/or the displacement mechanism can be connected conjointly and releasably to the patient fastening member by way of the releasable connection, and accordingly be removed and reinserted as a complete unit, if required. As a result thereof, temporary access for other instruments on the patient can be provided, for example, without the patient fastening member having to be released from the patient first. Moreover, the releasable connection permits the fast removal of parts of the positioning device in the event of complications, even while the instrument may still remain in the patient.

According to an advantageous design embodiment of the invention it is provided that the positioning device has an instrument advancing mechanism by way of which the instrument holder is displaceable along the holding axle of the positioning device relative to the patient fastening member, the rotary mechanism, the pivoting mechanism and/or the displacement mechanism. This has the advantage that the positioning device also facilitates manual or automated advancing of the instrument by means of the instrument holder in such a way that precise and reproducible advancing movements are possible. An advancement of the instrument, or of the instrument holder, along the holding axle can in particular be generated by the instrument advancing mechanism. For example, an instrument configured as a needle can in this instance be introduced along the desired spatial angular position and at a desired position into the patient. The holding axle herein forms a displacement axis for the instrument member, and an additional, third translatory degree of freedom is introduced in this way. The angular position of the holding axle in relation to the axis orthogonal to the patient holding surface herein can be adjusted by the pivoting mechanism.

The adjustment of the desired angular positions and/or displaced positions in the individual degrees of freedom of the positioning device can be carried out manually by adjustment elements on the positioning device, for example, or automatically by corresponding actuators disposed on the positioning device. Particularly advantageous herein is a remote-control capability for the adjustment of the individual degrees of freedom, e.g. for the use of the positioning device in a magnetic resonance tomography apparatus or a computer tomography apparatus.

According to an advantageous design embodiment of the invention it is provided that the rotary mechanism, the pivoting mechanism, the displacement mechanism and/or the instrument advancing mechanism have/has a cable pull mechanism for adjusting the instrument holder in at least one degree of freedom. The cable pull mechanism has the advantage that the positioning device is able to be remote-controlled by means of one or a plurality of traction cables of the cable pull mechanism, while the positioning device per se can be of a very compact design in terms of construction. In order for the medical object, or the base body, to be precisely adjusted in the potential degrees of freedom, the user therefore does not have to work within the MRT tunnel, but can operate the at least one traction cable from outside. Each traction cable, or each cable pull mechanism, can also be activated by way of automatically activatable actuators, for example in a computer-controlled manner.

A further advantage of the invention is that such an adjustment mechanism can be designed so as to be MRT-compatible throughout, because the cable pull mechanism can be implemented without any metal parts, for example, or similar. The required traction cable can be, for example, a plastic cable or a cable having a surface treated with a lubricant (e.g. wax); and the cable sleeve for guiding the traction cable can be a stronger plastics material hose (e.g. a PTFE hose). The positioning device according to the invention, which may also be referred to as a micropositioning system, is thus suitable for aligning and guiding medical objects of any type, in particular minimally invasive instruments which are used in interventional MRT.

By means of the invention, the positioning of the medical object is able to be remote-controlled in such a way that the positioning is readily possible at a distance even with little available space. In this way, the positioning device can be remotely operated in a substantially more user-friendly and comfortable manner.

The positioning device, in particular the at least one cable pull mechanism, can be manually operated, for example. For example, the cable of the cable pull mechanism can be pulled by hand. For locking in a desired position, the cable can then be fixed, for example using a customary cable pull fixing element such as, for example, a clamp or a cable clamp.

For the adjustment of a degree of freedom, the cable pull mechanism can have a common cable which can transmit sufficient activation forces in the pulling direction as well is in the pushing direction. A cable which can only transmit the activation forces in the pulling direction can also be used. In this instance, there may be a spring mechanism for the thrust direction, by way of which an automatic reset counter to the tensile force of the cable is performed, for example. The reset in the opposite direction can be performed by a spring reset element, for example. It is also possible to configure a cable pull mechanism with two counter-running traction cables, whereby a movement in the one direction of the respective degree of freedom takes place by pulling on the one traction cable, and a movement in the opposite direction takes place by pulling on the other traction cable. A spring reset element is not mandatory in this case.

According to an advantageous design embodiment of the invention it is provided that the at least one cable pull mechanism has a multifilament cable as the traction cable. This has the advantage that an MRT-compatible traction cable with little elasticity can be used. The traction cable can be configured as a braided cable, for example. Alternatively, a monofilament traction cable can also be used if the latter meets the requirements.

According to an advantageous design embodiment of the invention it is provided that the positioning device has a remote-controlled drive for at least one cable pull mechanism. This permits the positioning device to be easily operated at a distance.

According to an advantageous design embodiment of the invention it is provided that the positioning device has an electric-motor drive as the drive for at least one cable pull mechanism. This has the advantage that a very precise automatic adjustment of the respective positioning degrees of freedom of the positioning device can be carried out. In particular, no manual adjustment is required for this purpose, so that no operating personnel, or fewer operating personnel, is required. The input of control commands for the electric-motor drives can take place, for example, by means of an input into a control program by keyboard, PC mouse, controller (as known from video game consoles), gesture control and/or voice commands.

Alternatively, pneumatic motors, servo motors, piezo motors, or similar, may also be used as the drive for the cable pulls.

According to an advantageous design embodiment of the invention it is provided that the electric-motor drive has an electrically controllable stepper motor which by way of a worm gear is coupled to a cable drum to which is fastened at least one cable of a cable pull mechanism. This allows a very precise adjustment of the positioning device in the respective degrees of freedom, and likewise a higher reproducibility of the positioning actions. It can be implemented by such a worm gear that the arising cable forces are decoupled from the electric motor, and a self-locking mechanism is implemented when the motors are switched off. Moreover, a high reduction ratio can be implemented, this enabling a precise micropositioning of the instrument.

Alternatively, the cable drum can be connected directly to the motor in order to be able to utilize the cable forces as "force feedback" by evaluating the motor current, the latter increasing proportionally to the cable forces.

According to an advantageous design embodiment of the invention it is provided that integrated in at least one component of the positioning device is a transmitter and/or receiver coil for generating and receiving fields arising during the MRT examination. This has the advantage that, depending on the type of intervention, a defined setup in a predefined workflow can already be completely available to the user, and a required transmitter and/order receiver coil does not have to be separately placed on the patient first, but is already disposed on the patient as a result of the positioning device having been attached.

According to an advantageous design embodiment of the invention it is provided that the patient fastening member and/or the instrument guide sleeve have/has a plurality of marker elements which are/is identifiable during magnetic resonance tomography examinations and/or computed tomography examinations. This has the advantage that the correct positioning of the positioning device on the patient can be verified in the magnetic resonance tomography or computed tomography images. Moreover, referencing of the positions of the positioning device on the patient can be carried out automatically by automatic image processing, and further parameters for the examination or treatment of the patient can be automatically calculated as a result, e.g. the required adjustments of the positioning device in the various degrees of freedom for carrying out a specific procedure on the patient.

In this way, the invention achieves the potential for instruments to be more precisely aligned in such a way that even smaller target regions on the patient can be reached more precisely. Moreover, the quality of tomography-supported, minimally invasive interventions can be increased.

The electro-motor drives of the cable pulls can be precisely controlled by a control unit which carries out a control program, for example. In this way, remote-controlled alignment of the instrument by means of the positioning device 1 is possible. Elongations of the cable, which may arise, can be taken into account by the software and compensated for upon calibration, i.e. a calculated compensation of the distortion and the cable tension can be carried out.

The operation of the electric-motor drives can take place, for example, by means of a graphic user interface in the context of digital remote control, or fully automatically, e.g. by integrating the motor controller in a planning software for planning the medical intervention.

In this way, a complete micropositioning system can be provided. The micropositioning system is primarily provided for aligning and guiding instruments which are used in a minimally invasive manner (e.g. biopsy needles, RF electrodes) in iMRT. Alternatively, said micropositioning system can also be used in iCT (interventional computed tomography), whereby only the MRT marker elements have to be replaced by X-ray markers.

Upon manually placing the instrument approximately above the intended puncture location, the process of aligning the instrument fundamentally proceeds in such a way that the instrument in the context of planning an intervention is pivoted into the image layer which has previously been individually adjusted and optimally depicts, for example, the interventional target region and the desired puncture location. The subsequent puncture duct (trajectory) in the case of a minimally invasive invention is derived from the imaginary path between the puncture location and the target region.

The primary characteristic of the micropositioning system is its remote-control capability which makes it possible that, for example, according to corresponding results of a registration algorithm and along a preselected intervention trajectory, an instrument on the patient and in the tunnel of the MRT is aligned during iMRT in a completely remote-controlled manner sequentially under almost real-time imaging. The alignment of the instrument can take place either purely manually, in a partially automated manner (e.g. by way of a manually controlled remote-control operation, e.g. pushing keys on a suitable operating element/hand-held controller), or in a fully automatic, software-controlled (=robotic) manner, in accordance with the degree of the technical equipment of all system components.

Furthermore, the micropositioning system not only makes it possible that the instrument is simply aligned along a preselected, interventional trajectory just above the skin surface, but also that said instrument is completely advanced to the target region (e.g. suspected tumor in the prostate gland or in the lung), including the subsequent retrieval of the instrument. In this way, the intervention in its entirety can also take place fully automatically (robotically) in the context of a minimally invasive intervention.

In this instance, the user no longer has to work directly in the intervention region by means of a stretched-out arm in the tight and poorly accessible center of the MRT tunnel, but can actively control the intervention and simultaneously monitor the latter on a screen by means of the real-time images even at a relatively far distance (e.g. in the control room), depending on the degree of automation and the control installations.

All the kinematics of the positioning device can be operated from a distance in a precise and play-free manner by means of the cable pull mechanisms, in particular when all movable components are able to be operated by preloaded cable pulls which act in a mutually complementary manner.

The positioning device can be designed to be compact, lightweight and space-saving in such a way that the positioning device can also be used in tight conditions, e.g. in magnetic resonance tomography apparatuses. The positioning device herein permits five remote-controlled degrees of freedom in terms of adjustment.

No additional infrastructure apart from a medical imaging system is required on site, as opposed to pneumatic systems which require a compressed-air supply, for example.

The positioning device can be provided in a relatively cost-effective manner, whereby many parts of the positioning device can be provided as, for example, plastic components. Therefore, the positioning device can be provided as a single-use product.

Partially automated or fully automated aligning of the instruments and advancing of the instruments is possible. Therefore, fully automatic puncturing can be carried out on the patient with the aid of planning data.

The invention will be explained in more detail hereunder by means of exemplary embodiments and with the use of drawings.

DETAILED DESCRIPTION OF THE INVENTION

Figure 1:
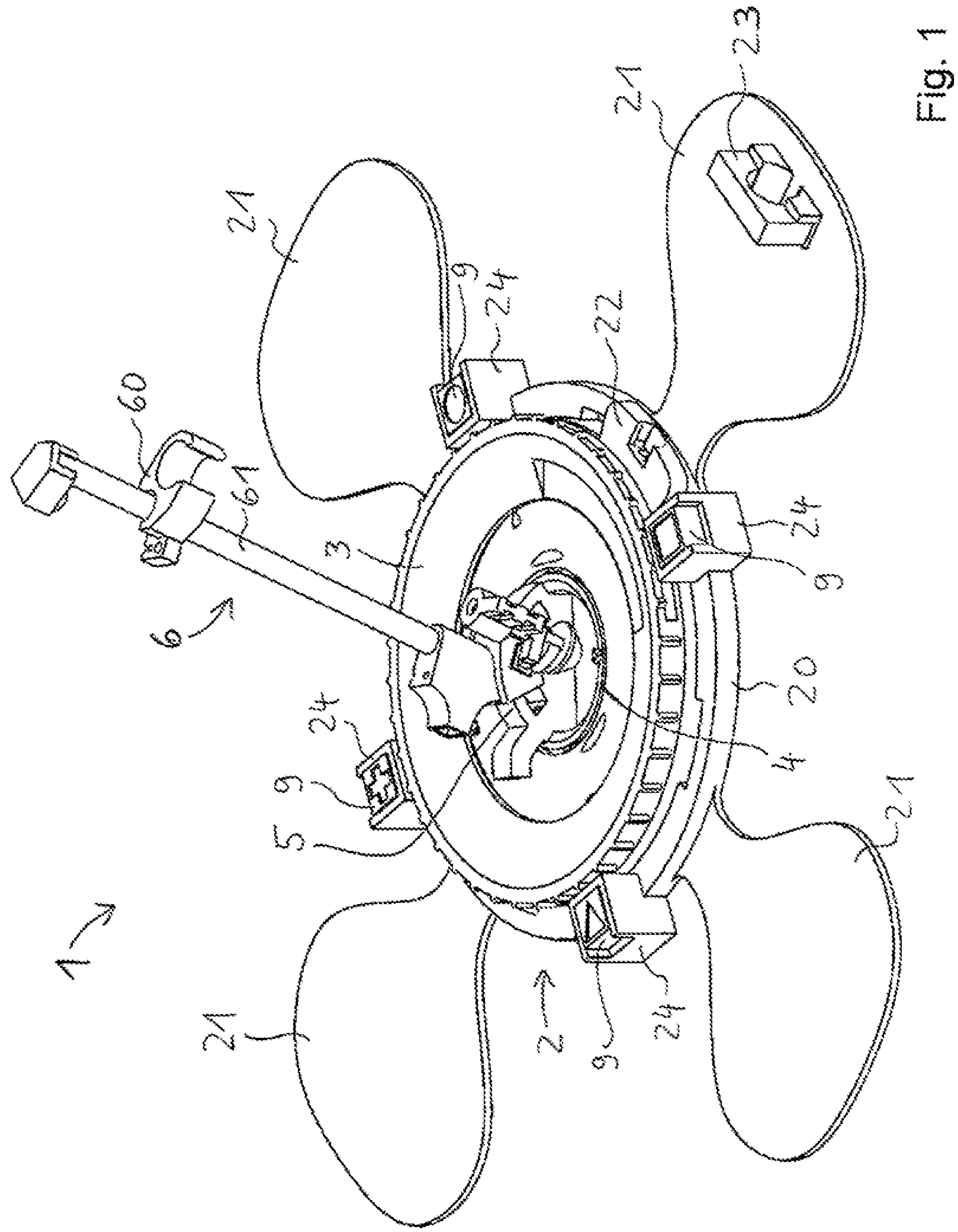
FIGS. 1, 2 show a positioning device in perspective view.

The positioning device 1 which can be seen in FIG. 1 has a patient fastening member 2 which is specified to fasten the positioning device 1 to the patient. Fastened to the patient fastening member 2 is an instrument alignment unit which is adjustable in various degrees of freedom and has a displacement mechanism 3, a rotary mechanism 4 and a pivoting mechanism 5. An instrument mounting 6 is fastened to this instrument alignment unit, an instrument holder 60 being in turn fastened to said instrument mounting 6. The instrument holder 60 serves for holding a medical instrument. The instrument can be, for example, a biopsy needle, a catheter, an endoscope or an RF absorption instrument. The medical instrument can be, for example, latched, snap-fitted, or fixedly clamped to the instrument holder. The instrument mounting 6 has an instrument advancing mechanism by way of which the instrument holder 60 is displaceable in a reciprocating manner along a holding axle 61.

The patient fastening member 2 has a main body 20. For fastening to the patient, the patient fastening member 2 has a plurality of fastening surfaces 21 which protrude from the external circumference of the main body 20 and which can be configured as self-adhesive fastening surfaces, for example. Moreover, a plurality of mountings 24 for receiving marker elements 9 are disposed on the patient fastening member 2, in particular on the main body 20. The marker elements 9 can be identified in magnetic resonance tomography or computed tomography examinations. Furthermore, the patient fastening member 2, or a part connected thereto, has a central guide 22 for conjointly guiding a plurality of cables of cable mechanisms, by way of which the various adjustment possibilities of the positioning device 1 can be adjusted. The cables can be guided centrally by way of a common sleeve, i.e. a central tube. The central tube can be configured, for example, as a tube or hose. The patient fastening member 2 can additionally have a fixing element 23 by way of which the sleeve can be fastened to the positioning device 1 in a defined manner.

The patient fastening member 2 has a patient holding surface for bearing on patients, which can be formed by the lower side of the main body 20 that faces the patient. This patient holding surface forms a reference plane (X-Y-plane) for a coordinate system relating to the positioning device.

Figure 2:
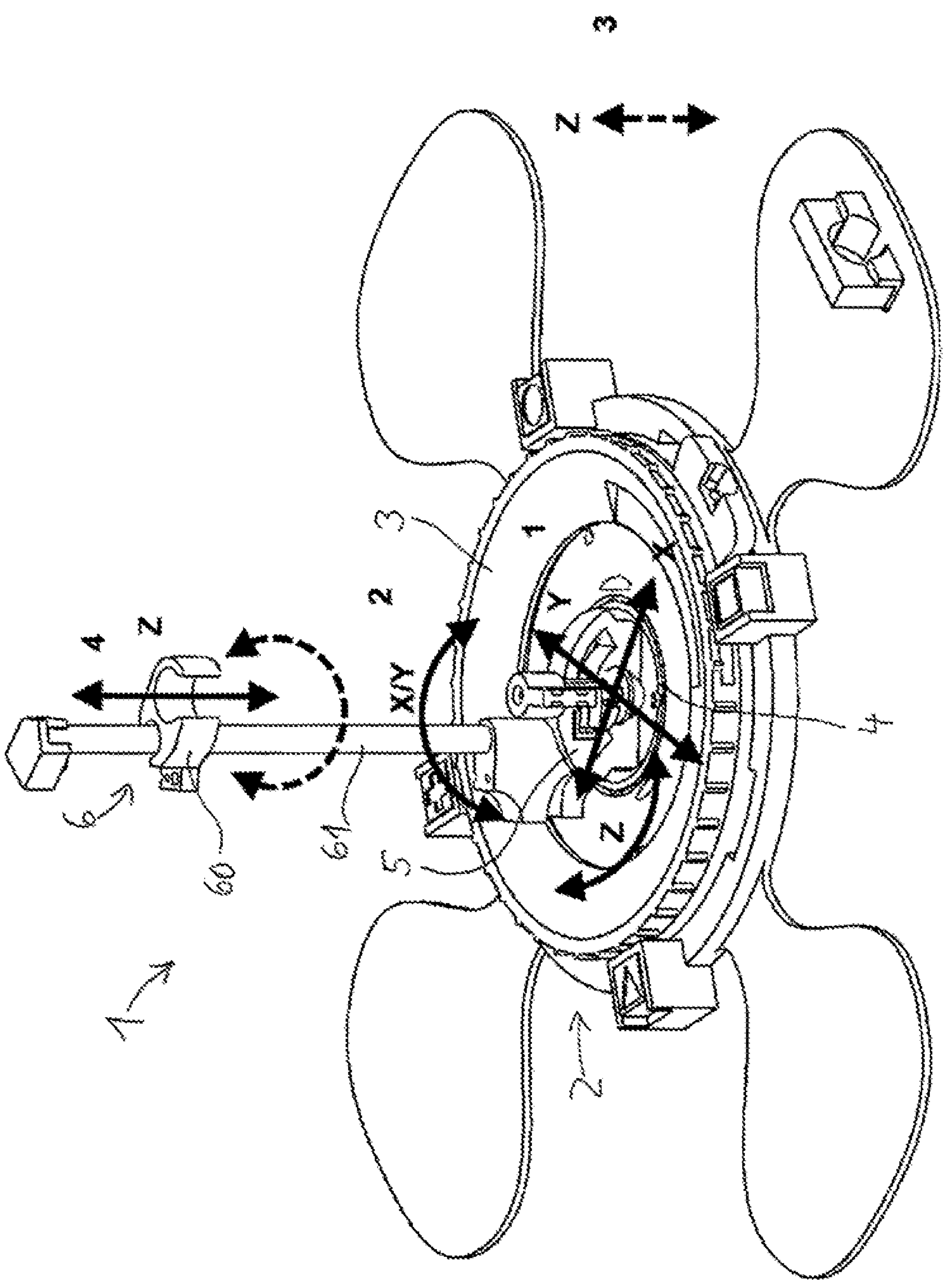

The various adjustment degrees of freedom of the positioning device are to be explained by means of FIG. 2. The instrument holder 60 can be displaced in an X-Y-plane parallel to the patient holding surface by way of the displacement mechanism 3. The instrument holder 60 can be twisted about an axis orthogonal to the patient holding surface, i.e. an axis (Z-axis) orthogonal to the X-Y-plane, by way of the rotary mechanism 4. The instrument holder 60 can be adjusted in terms of the angular position in relation to the patient holding surface, i.e. in relation to the X-Y-plane, by way of the pivoting mechanism 5. The instrument holder 60 can be adjusted along the holding axle 61 by the instrument advancing mechanism.

Figure 3:
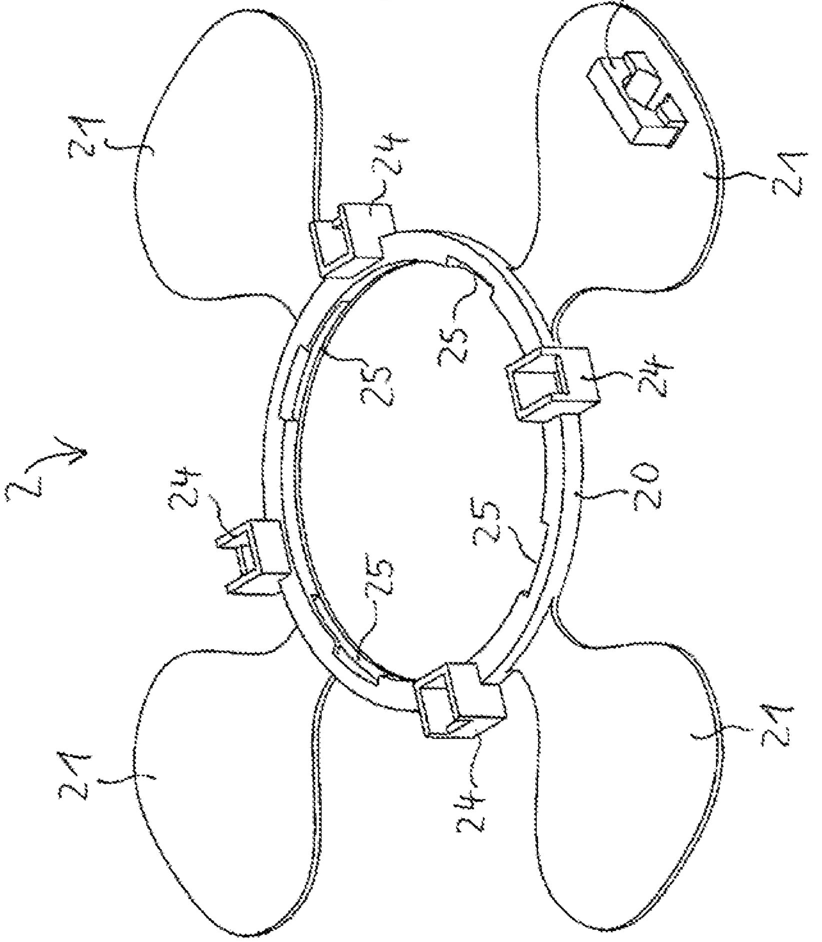
FIG. 3 shows a patient fastening member of the positioning device.

FIG. 3 shows the patient fastening member 2 as an individual component. Receptacle elements 25 which serve for receiving protrusions 31 of a base body 30 of the displacement mechanism 3 and are configured on the internal circumference of the main body 20 can be seen. The receptacle elements 25, conjointly with the protrusions 31, form a type of bayonet fastening, for example, which permits the instrument alignment unit and the further parts fastened thereto, including the instrument holder 60, to be removed from the patient fastening member 2 as desired or permits said instrument holder 60 to be fastened thereon in a simple manner.

The components can be gently released from the patient fastening member 2 by the bayonet connection. Risks caused by mechanical stress in the intervention region, e.g. by releasing the fastening surfaces 21 from the patient, are avoided. The instrument alignment unit herein can be temporarily removed from the patient in a simple manner, and subsequently be placed in the same position again in a reversible manner.

Additionally, a transmitter and/or receiver coil for generating and receiving fields that arise in the MRT examination can be integrated in the main body 20 or the base body 30. As a result, magnetic resonance tomography examinations can be carried out in a more efficient and more effective manner. No external surface coils have to be placed and positioned separately on the patient during the preparation process in order to obtain positive and defined imaging. Moreover, such an integrated transmitter and/or receiver coil prevents that the adjustment kinematics of the positioning system may be disturbed by externally placed coils.

Figure 4:
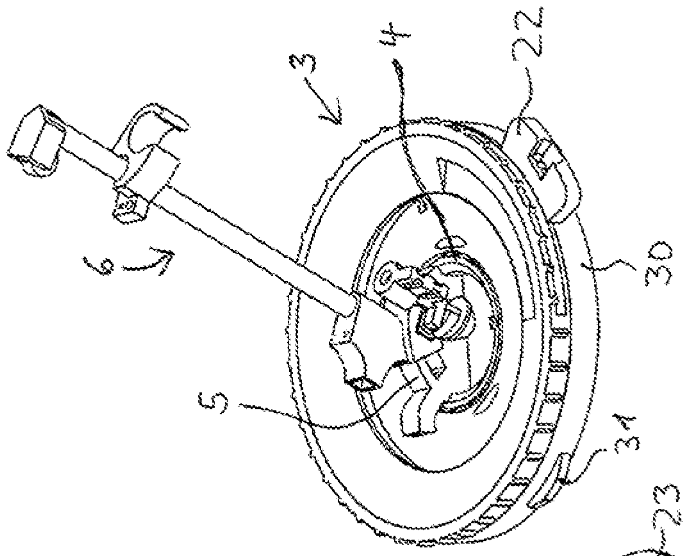
FIG. 4 shows elements of the positioning device which are to be fastened to the patient fastening member.

FIG. 4 shows the unit consisting of the displacement mechanism 3, the rotary mechanism 4, the pivoting mechanism 5 and the instrument mounting 6 when removed as a unit from the patient fastening member 2. The protrusions 31 which are configured for insertion into the receptacle elements 25 of the patient fastening member 2 and on the external circumference protrude from the base body 30 of the displacement mechanism 3 can be seen in particular.

Figure 5:
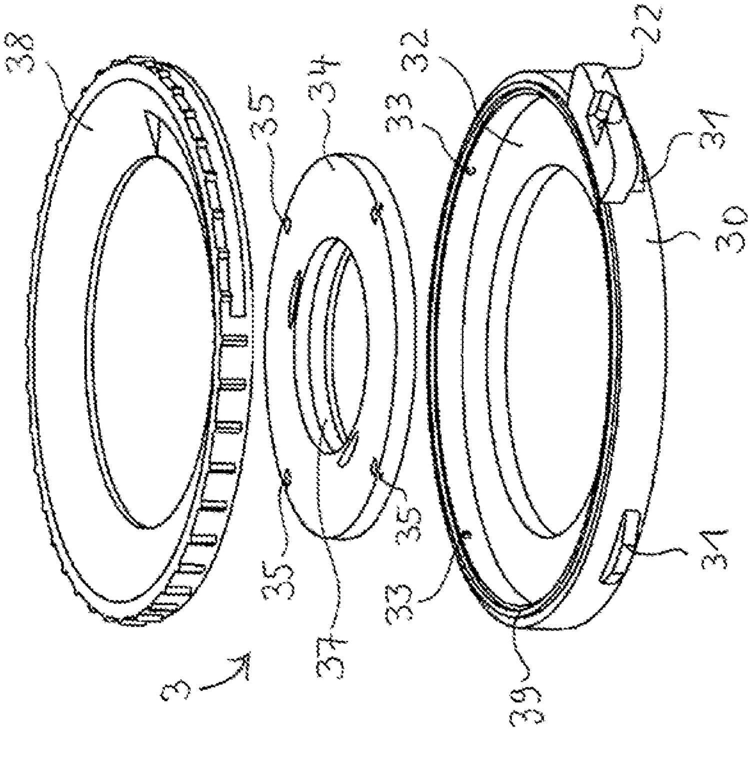
FIG. 5 shows a displacement mechanism of the positioning device in an exploded illustration.

FIG. 5 shows the displacement mechanism 3 having the individual construction elements thereof. The base body 30 of the displacement mechanism 3, already mentioned, has an internal receptacle region 32 in which a displacement member 34 can be received. The receptacle region 32 has a significantly larger diameter than the external diameter of the displacement member 34. This makes it possible for the displacement member 34 to be displaced to a certain extent in the X-direction and Y-direction within the receptacle region 32. The displacement member 34, which is disposed in the receptacle region 32, is covered by an upper closure member 38 and in this way is fixed in the Z-direction in the receptacle region 32 of the base body 30, but is displaceable in the X-direction and Y-direction, as has been mentioned.

The displacement member 34 has holding elements in anchoring points 35 for fastening cables of cable pull mechanisms. Corresponding conduit openings 33 and guide grooves 39 for guiding the cables are disposed on the base body 30. As a result, the cables are guided to the central guide 22.

The displacement member 34 moreover has an inner receptacle space 37 in which the further elements of the positioning device 1, in particular parts of the rotary mechanism 4, can be fastened.

Figure 6:
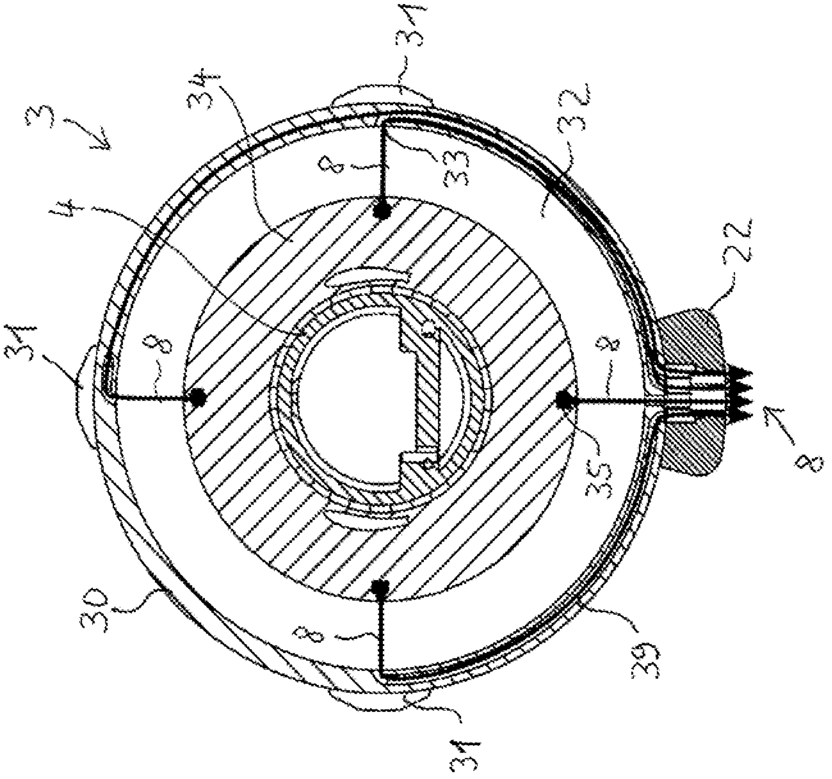
FIG. 6 shows a sectional view of the displacement mechanisms.

FIG. 6 shows the arrangement of the displacement member 34 in the receptacle region 32. To be seen in particular are the attachment and the guiding of four cables 8 which are fastened to four holding elements in the anchoring points 35 of the displacement member 34 and guided by the conduit openings 33 and the guide grooves 39 to the central guide 22, said holding elements being circumferentially spaced apart in a uniform manner. By pulling on in each case one pair of opposite counter-running cables 8, the displacement member 34 can thus be selectively displaced exclusively in the X-direction or in the Y-direction, or in combination in the X-Y plane.

Figure 7:
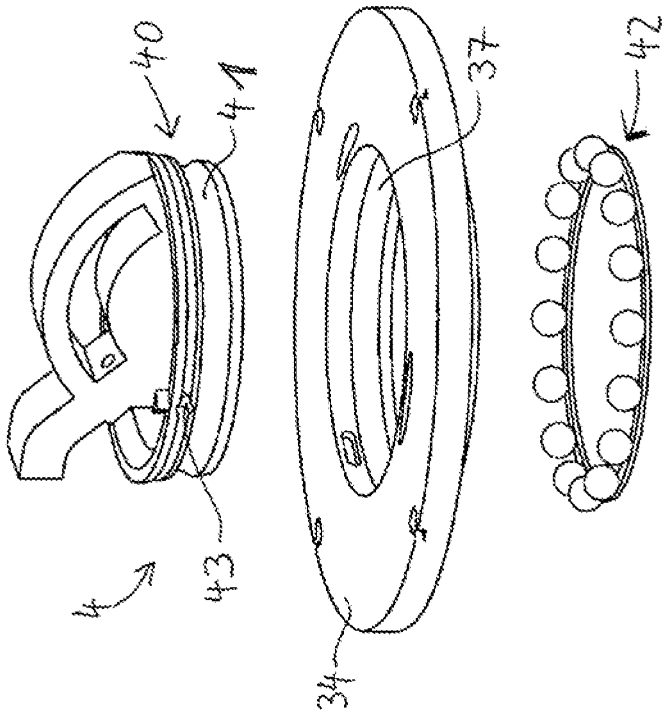
FIG. 7 shows a rotary mechanism of the positioning device in an exploded illustration.

FIG. 7 shows parts of the rotary mechanism 4. A receptacle portion 41 which serves for insertion into the receptacle space 37 of the displacement member 34, which is shaped as a mating piece, is configured on a main body 40 of the rotary mechanism 4. The main body 40 can be fastened to the displacement member 34 by way of the receptacle portion 41, e.g. by way of a plain bearing, as a result of which said main body 40 is able to be twisted about the Z-axis. FIG. 7 shows an advantageous design embodiment of a connection between the main body 40 and the displacement member 34 by way of a roller bearing 42, e.g. a ball bearing. In order to guarantee compatibility of the positioning device with MRT and CT examinations, all of the parts of the positioning device can be formed so as to be metal-free, e.g. be made of plastics material or glass. The rolling members of the roller bearing 42 can be configured as glass members, for example.

Figure 8:
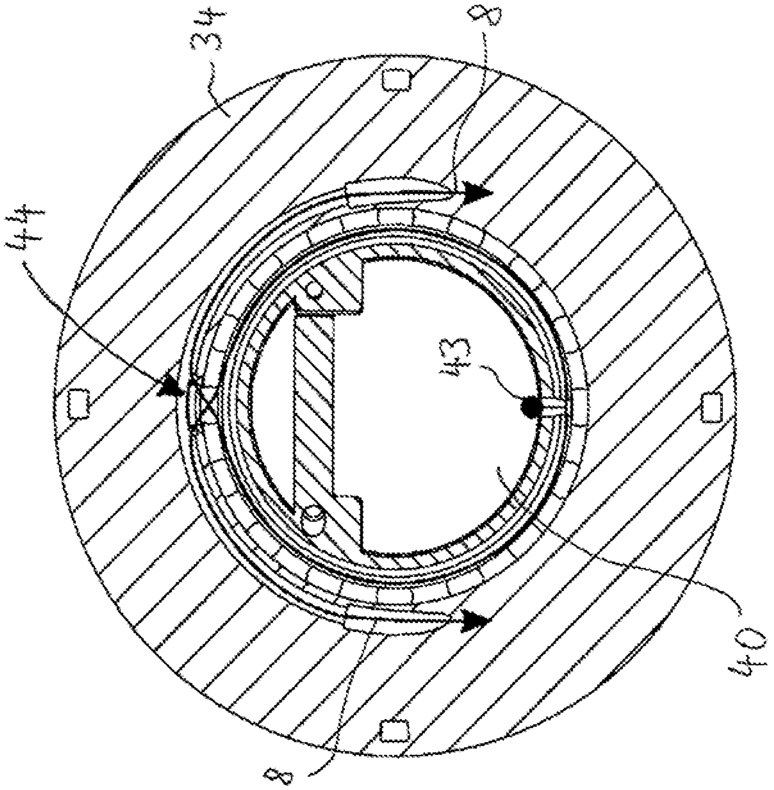
FIG. 8 shows a rotary mechanism in a sectional illustration.

Holding elements 43 for anchoring cables of cable pull mechanisms are disposed on the main body 40. FIG. 8 shows the articulation of the rotary mechanism 4 by way of two cables 8 operating in a counter-running manner. Both cables 2 can be fastened to a holding element in an anchoring point 43 of the main body 40. As is illustrated by way of example, the cables 8 can cross one another at a crossing 44. A maximum twisting angle of the rotary mechanism 4 of ±180° can be implemented in this way.

Figure 10:
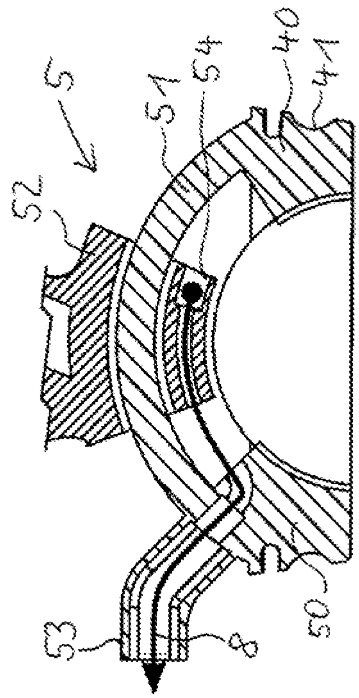
FIGS. 10, 11 show the pivoting mechanism in a sectional illustration.
Figure 11:
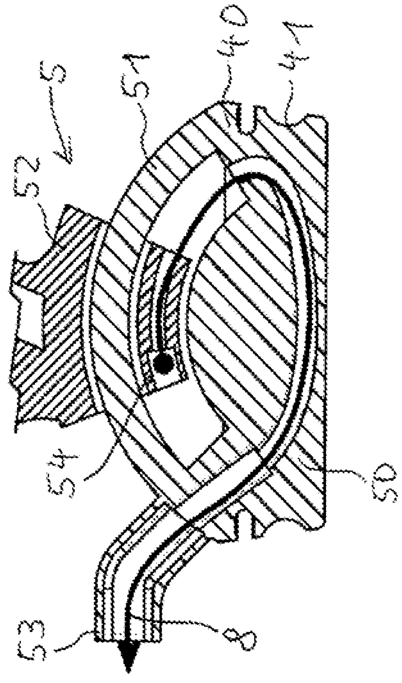
Figure 9:
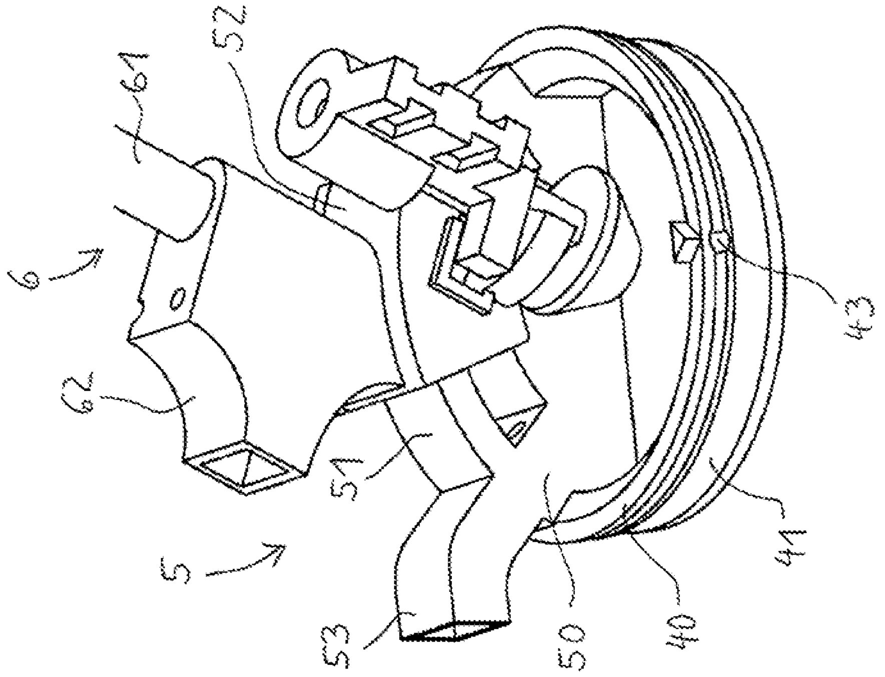
FIG. 9 shows a pivoting mechanism of the positioning device.

FIG. 9 shows the pivoting mechanism 5. The pivoting mechanism 5 has a base body 50 which can be connected to the main body 40 of the rotary mechanism 4, for example, or be configured so as to be integral to the latter. A mounting 51 which runs in an arcuate manner and on which a pivoting element 52 is pivotably mounted is disposed on the base body 50. The pivoting element 52 can be moved in a reciprocating manner along the arcuate mounting 51, which leads the instrument mounting 6 and thus the instrument holder 60 to pivot in relation to the X-Y-plane. As is shown in FIGS. 10 and 11, one or a plurality of holding elements 54 for anchoring cables of cable pull mechanisms can be disposed on the pivoting element 52. For example, two counter-running cables 8 can again be fastened thereto. The cables 8 can be routed out of a cable exit 53 of the base body 50 by way of corresponding cable guide ducts, and be activatable from there. For example, pivoting of the instrument mounting 6 by ±45° relative to the Z-axis can be performed by the pivoting mechanism.

Figure 12:
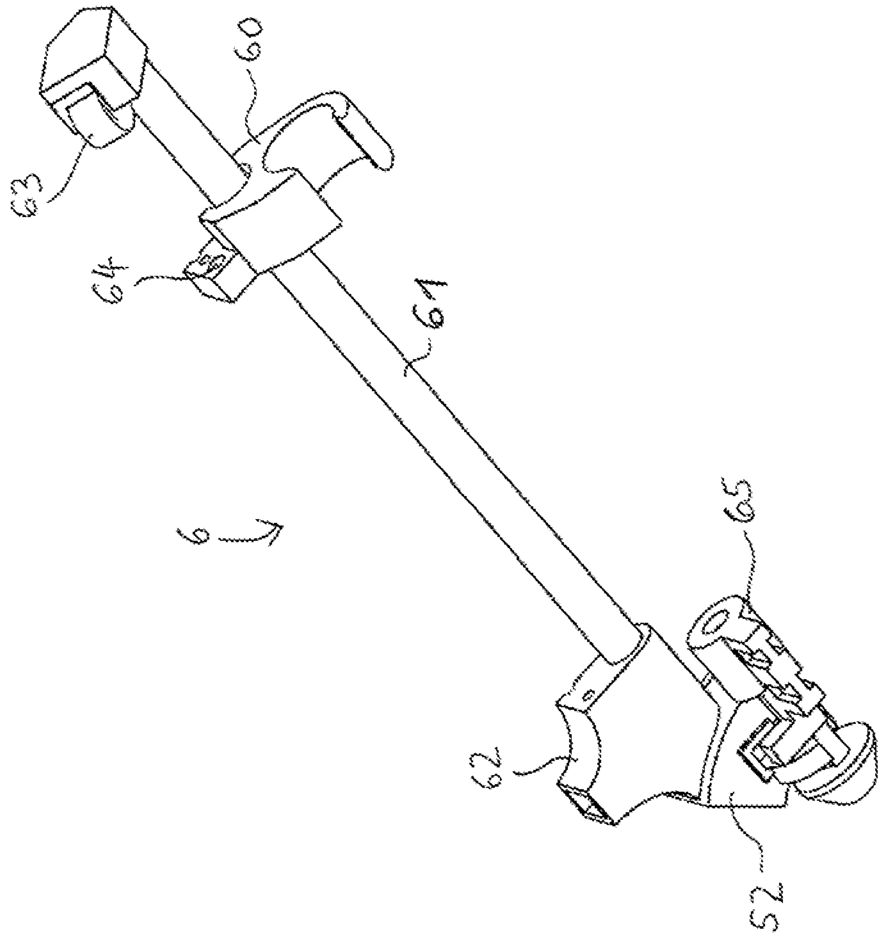
FIG. 12 shows an instrument holder in a perspective view.

FIG. 12 shows the instrument mounting 6. The instrument mounting 6 has the holding axle 61 which has already been mentioned and can be fastened to the pivoting element 52 by way of a fastening member 62, for example. The instrument holder 60 is mounted so as to be displaceable on the holding axle 61. Cable guiding and fastening elements 64 are disposed at c. A deflection element 63 which serves for deflecting at least one cable of a cable pull mechanism is situated on the holding axle 61, at that end that faces away from the fastening member 62. The deflection element 63 can be a ceramic member, for example, which can be configured as a cable pulley or deflection roller. An instrument advancing mechanism is implemented by the cable guiding and fastening elements 64 and the deflection element 63.

Figure 13:
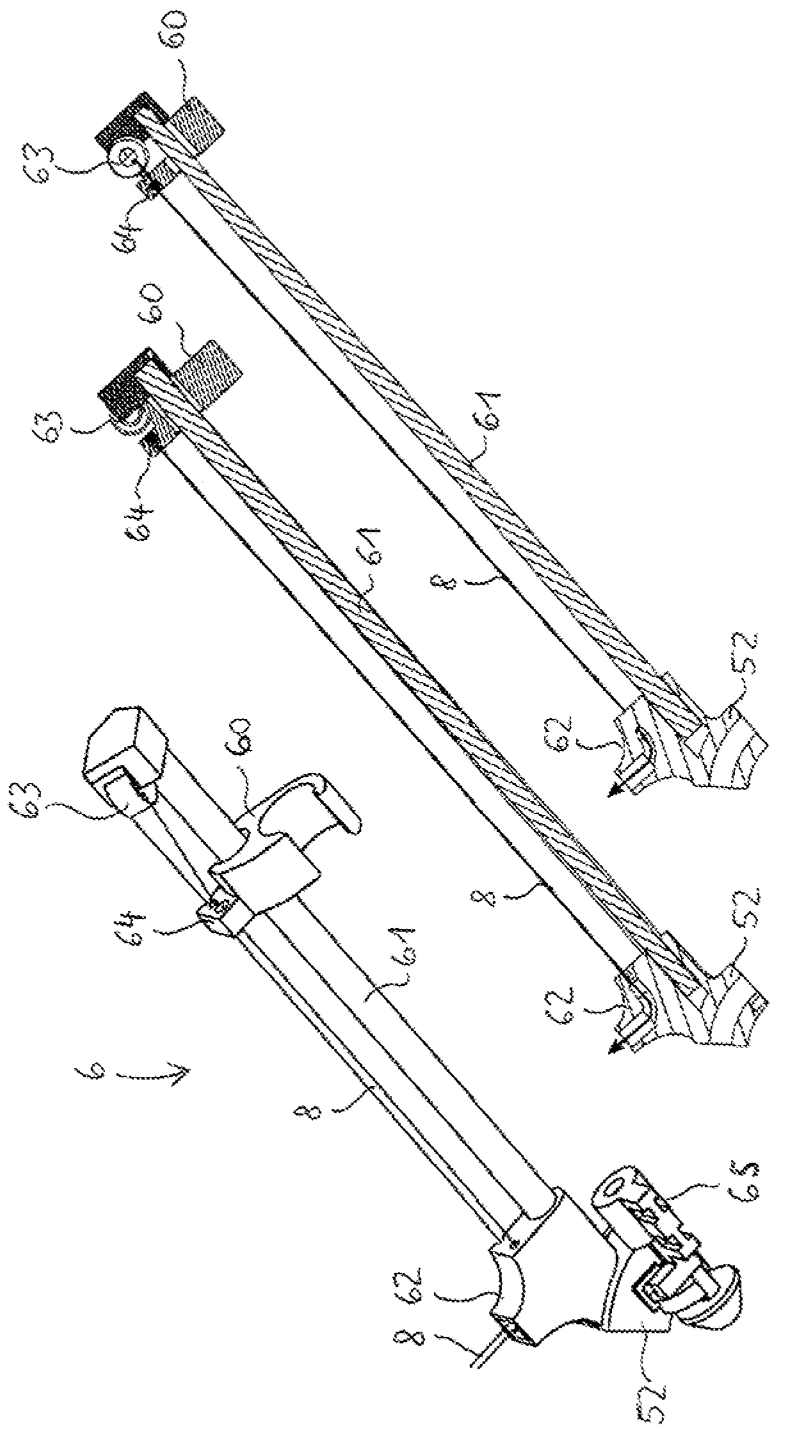
FIG. 13 shows the instrument holder having an instrument advancing mechanism in a perspective view, and in two sectional views.

FIG. 13 shows the instrument mounting 6 having counter-running cables 8 which are disposed thereon and serve for activating the instrument holder 60 for displacement. Both cables 8 are fastened to the cable guiding and fastening elements 64. One cable is deflected by the deflection element 63 and is additionally guided through a guide opening of the cable guiding and fastening elements 64. Both cables 8 are guided through the fastening member 62 and exit at a common exit location.

Moreover, an instrument guide sleeve 65 is disposed so as to be lockable on the pivoting element 52 or the fastening member 62. The instrument guide sleeve 65 serves for precisely guiding the medical instrument, which is fastened to the instrument holder 60, during a displacement of the instrument holder 60 along the holding axle 61. The instrument guide sleeve 65 can have one or a plurality of further markers. The instrument guide sleeve 65 can be unblocked and thus released from the pivoting element 52, or from the fastening member 62, by means of a rotating movement, if required.

Figure 14:
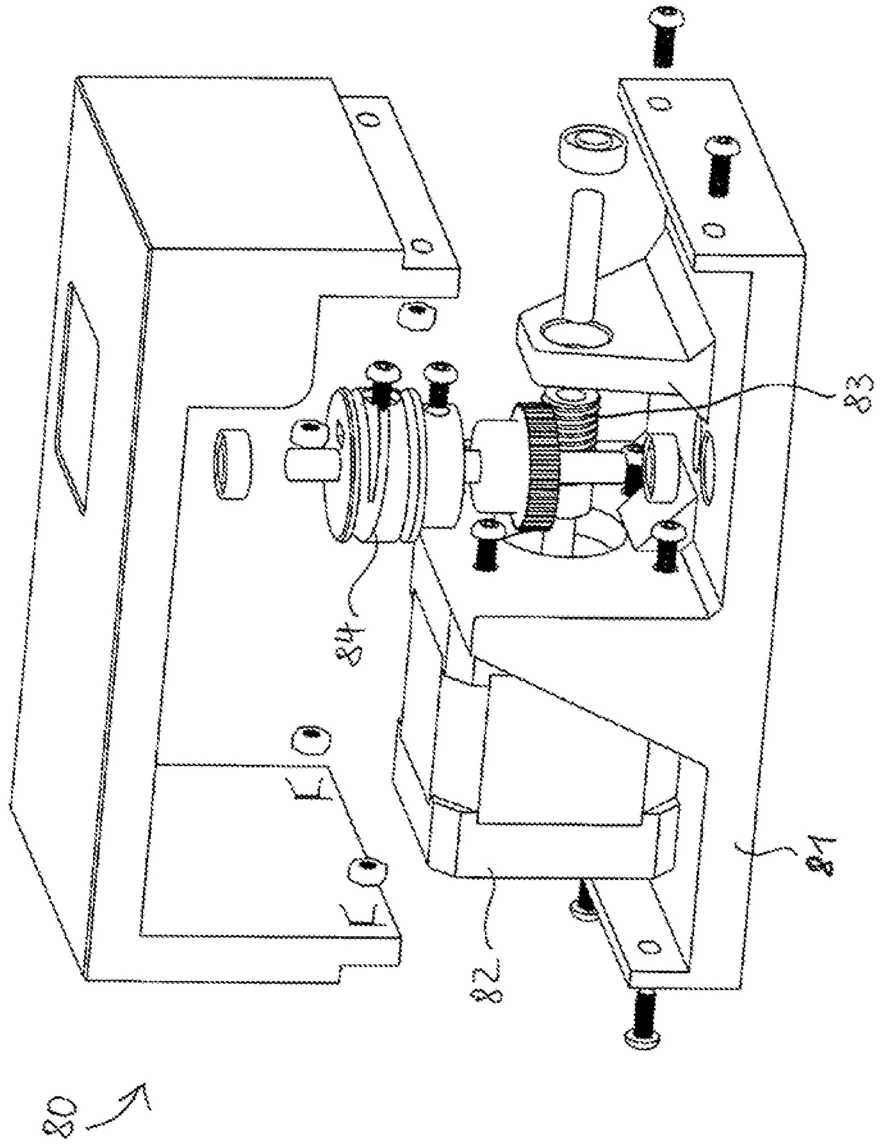
FIG. 14 shows an electric-motor drive in an exploded illustration.

FIG. 14 shows by way of example an electric-motor drive for activating a cable, or two counter-running cables, of a cable pull mechanism. The electric-motor drive 80 has a housing 81 in which is disposed an electrically controllable stepper motor 82. The stepper motor 82 is coupled to a cable drum 84 by way of a worm gear 83. The cable, or the cables, of the cable pull mechanism to be activated is/are fastened to the cable drum 84.

Figure 15:
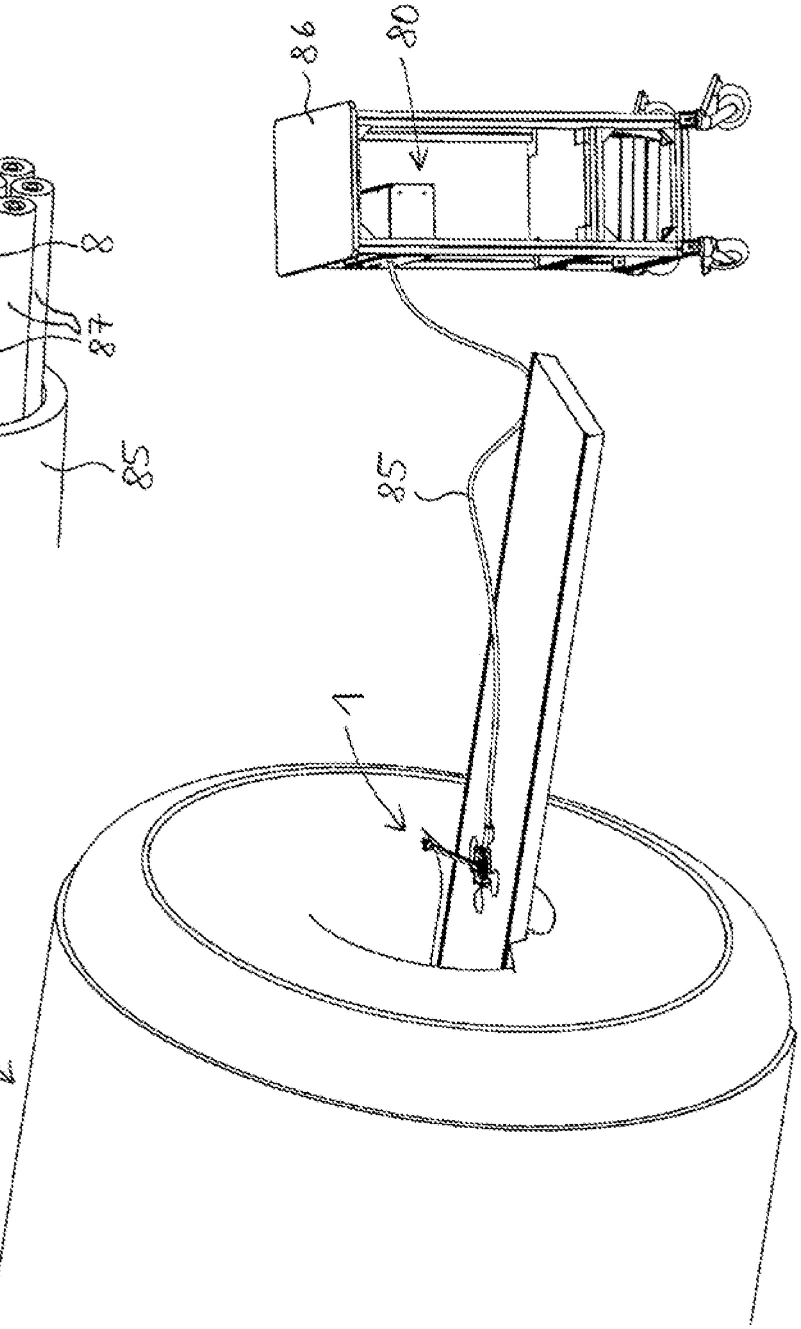
FIG. 15 shows the application of the positioning device on an MRT systems.

FIG. 15 shows the application of the positioning device 1 according to the invention on a magnetic resonance tomography apparatus 7. The positioning device 1, by way of the various cables of the cable pull mechanism that are guided in a central tube 85, is connected to a plurality of electric-motor drives 80. The electric-motor drives 80 can be disposed, for example, on a mobile drive system 86, for example a drive system which possesses rollers and as a result can be easily moved to the site of deployment by the user. Alternatively, stationary and floor-proximal fixing of the electric-motor drives 80 in the scanner room or else control room can also be provided, so that acceleration forces of the metallic elements, which may be created by the attraction forces of the magnetic field of the MRT and may injure patients or personnel, are absolutely precluded.

Figure 16:
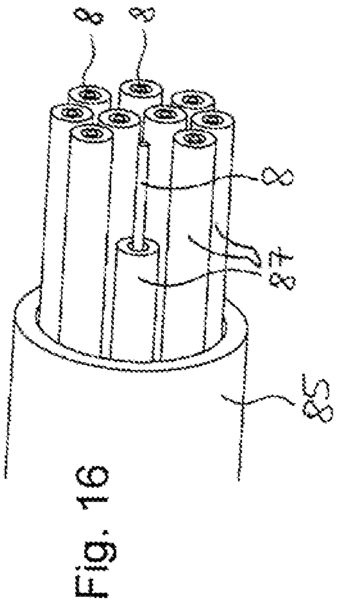
FIG. 16 shows an arrangement of the cable pulls in the central tube.

As is highlighted in FIG. 16, the cables 8 can in each case be guided separately in a dedicated sleeve 87, i.e. in the manner of a Bowden cable, at least in the region of the central tube 85. In this way, mutual influences of the cables 8 are minimized. The sleeve 87 can be, for example, a Teflon hose in order to minimize cable friction.

What is claimed is:

1. A positioning device for positioning a medical instrument relative to a patient comprising:

a patient fastening member configured to fasten the positioning device to the patient and including a patient holding surface for bearing on the patient, and an instrument holder including a rotary mechanism and a displacement mechanism, wherein the instrument holder is configured to:

hold the medical instrument, connect to the patient fastening member via the rotary mechanism, such that the instrument holder is mounted in an axis orthogonal to the patient holding surface so as to be rotatable relative to the patient fastening member, and couple to the patient fastening member via the displacement mechanism such that:

the instrument holder is displaceable in several directions in a plane parallel to the patient holding surface or in a spherically or cylindrically curved path, and the rotary mechanism is displaceable via the displacement mechanism in several directions.

2. The positioning device as claimed in claim 1, wherein the instrument holder is coupled to the patient fastening member via a pivoting mechanism by way of which the angular position of the instrument holder is adjustable in relation to the patient holding surface.

3. The positioning device as claimed in claim 2, wherein the pivoting mechanism, conjointly with the instrument holder, by way of the rotary mechanism is able to be twisted about the axis orthogonal to the patient holding surface relative to the patient fastening member.

4. The positioning device as claimed in claim 1, wherein the pivoting mechanism by way of the displacement mechanism is displaceable in one or a plurality of directions in the plane parallel to the patient holding surface.

5. The positioning device as claimed in claim 1, wherein the instrument holder, or a component of the positioning device that is connected thereto, is releasably connected to the patient fastening member by way of a releasable connection, in particular a bayonet connection.

6. The positioning device as claimed in claim 1, wherein the positioning device has an instrument advancing mechanism by way of which the instrument holder is displaceable along a holding axle of the positioning device relative to the patient fastening member, the rotary mechanism, the pivoting mechanism and/or the displacement mechanism.

7. The positioning device as claimed in claim 1, wherein the rotary mechanism, the pivoting mechanism, the displacement mechanism and/or the instrument advancing mechanism have/has a cable pull mechanism for adjusting the instrument holder in at least one degree of freedom.

8. The positioning device as claimed in claim 7, wherein the positioning device has a remote-controlled drive for at least one cable pull mechanism.

9. The positioning device as claimed in claim 7, wherein the positioning device has an electric-motor drive as the drive for at least one cable pull mechanism.

10. The positioning device as claimed in claim 9, wherein the electric-motor drive has an electrically controllable stepper motor which by way of a worm gear is coupled to a cable drum to which is fastened at least one cable of a cable pull mechanism.

11. The positioning device as claimed in claim 1, wherein integrated in at least one component of the positioning device is a transmitter and/or receiver coil for generating and receiving fields arising during the magnetic resonance tomography.

12. The positioning device as claimed in claim 1, wherein the patient fastening member and/or an instrument guide sleeve have/has a plurality of marker elements which are/is identifiable during magnetic resonance tomography examinations and/or computer tomography examinations.

* * * * *